(12) United States Patent
Franklin et al.

(10) Patent No.: US 10,345,621 B2
(45) Date of Patent: Jul. 9, 2019

(54) ELECTRONIC OPHTHALMIC DEVICE WITH EXTREME GAZE ANGLE DETECTION

(71) Applicant: Johnson & Johnson Vision Care, Inc., Jacksonville, FL (US)

(72) Inventors: Ross Franklin, Jacksonvile, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 15/439,149

(22) Filed: Feb. 22, 2017

(65) Prior Publication Data

US 2018/0239169 A1 Aug. 23, 2018

(51) Int. Cl.
| | |
|---|---|
| *G02C 7/08* | (2006.01) |
| *A61B 3/113* | (2006.01) |
| *G02C 7/04* | (2006.01) |
| *A61F 2/16* | (2006.01) |
| *A61F 2/14* | (2006.01) |
| *A61F 2/48* | (2006.01) |

(52) U.S. Cl.
CPC .............. *G02C 7/083* (2013.01); *A61B 3/113* (2013.01); *A61F 2/1451* (2015.04); *A61F 2/1624* (2013.01); *G02C 7/04* (2013.01); *G02C 7/081* (2013.01); *A61F 2002/482* (2013.01)

(58) Field of Classification Search
CPC .................. A61F 2/1451; A61F 2/1624; A61F 2002/482; A61B 3/113
USPC ....................... 351/159.3, 159.02, 159.01, 41
See application file for complete search history.

(56) References Cited

U.S. PATENT DOCUMENTS

| | | | |
|---|---|---|---|
| 4,702,573 A | 10/1987 | Morstad | |
| 6,851,805 B2 | 2/2005 | Blum | |
| 7,931,832 B2 | 4/2011 | Pugh | |
| 8,080,187 B2 | 12/2011 | Tepedino, Jr. | |
| 8,092,013 B2 | 1/2012 | Pugh | |
| 8,348,424 B2 | 1/2013 | Pugh | |
| 8,665,526 B2 | 3/2014 | Pugh | |
| 8,767,308 B2 | 7/2014 | Pugh | |
| 8,857,983 B2 | 10/2014 | Pugh | |
| 8,906,088 B2 | 12/2014 | Pugh | |
| 8,967,488 B2 | 3/2015 | Pugh | |
| 9,050,185 B2 | 6/2015 | Pugh | |
| 9,072,465 B2 | 7/2015 | Pugh | |
| 9,158,127 B2 | 10/2015 | Pugh | |
| 9,180,636 B2 | 11/2015 | Pugh | |
| 9,268,155 B2 | 2/2016 | Pugh | |
| 9,351,827 B2 | 5/2016 | Toner | |
| 9,442,310 B2* | 9/2016 | Biederman | G02C 7/083 |
| 9,442,311 B2 | 9/2016 | Yeager et al. | |

(Continued)

*Primary Examiner* — Tuyen Tra

(57) ABSTRACT

Disclosed are powered or electronic ophthalmic devices or lenses which can have the ability to monitor and sense extreme gaze angle. Also disclosed is the use of extreme gaze angles to control the focal state of the lens as well as for augmenting, control of, or input to, other device parameters of the powered or electronic ophthalmic lens. Applicants have researched and determined what are believed to be acceptable ranges of both upward and downward extreme gaze angles which are not only measurably distinguishable from normally occurring gaze angles associated with everyday activities, but which are still achievable by the wearer if purposeful, as they are still within human eye movement capability.

11 Claims, 13 Drawing Sheets

(56) References Cited

U.S. PATENT DOCUMENTS

| | | | |
|---|---|---|---|
| 2014/0243971 A1* | 8/2014 | Pugh | G02C 7/04 623/6.22 |
| 2017/0023793 A1 | 1/2017 | Shtukater | |
| 2017/0255025 A1* | 9/2017 | Gutierrez | G02C 7/021 |

* cited by examiner

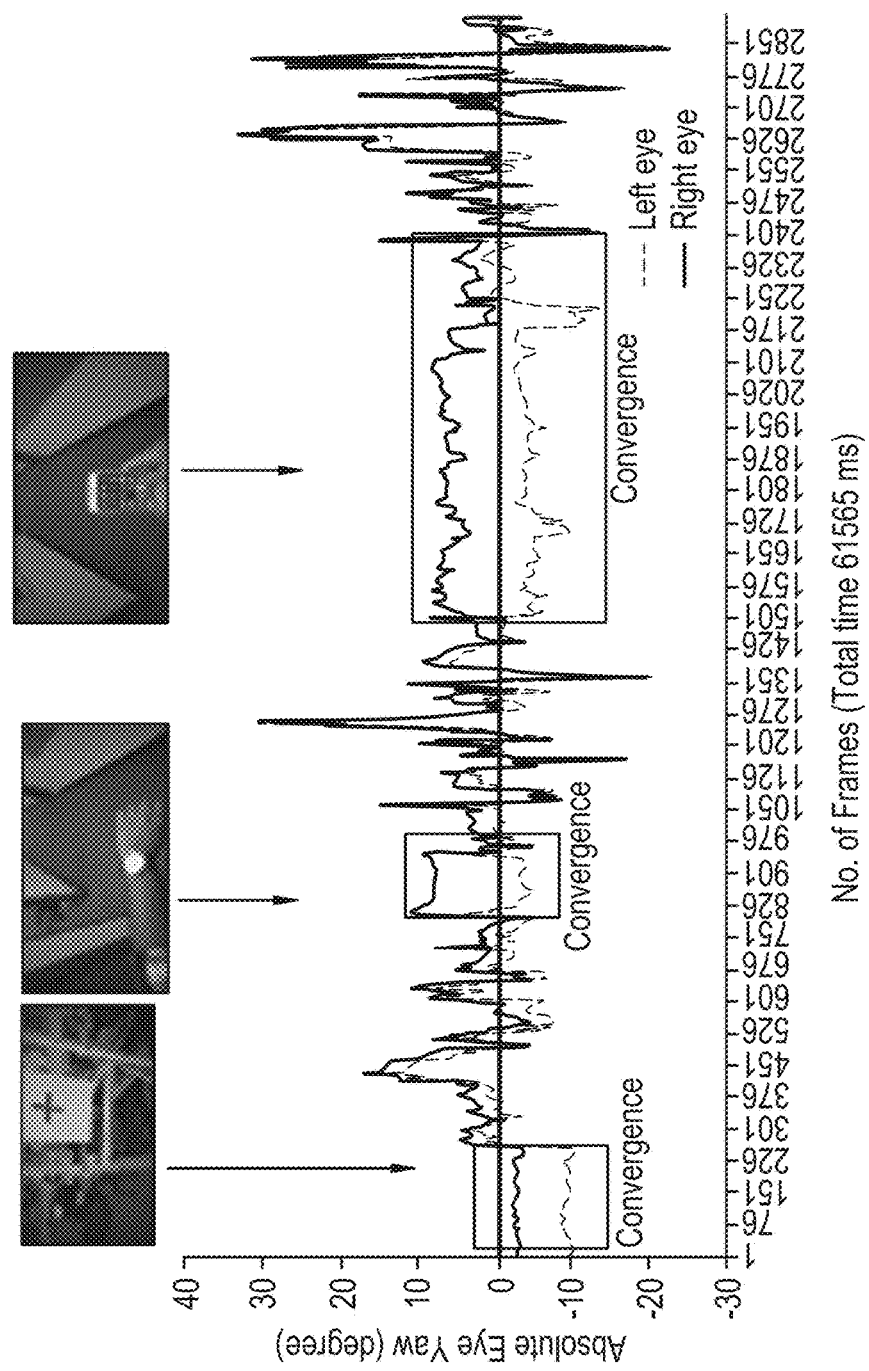

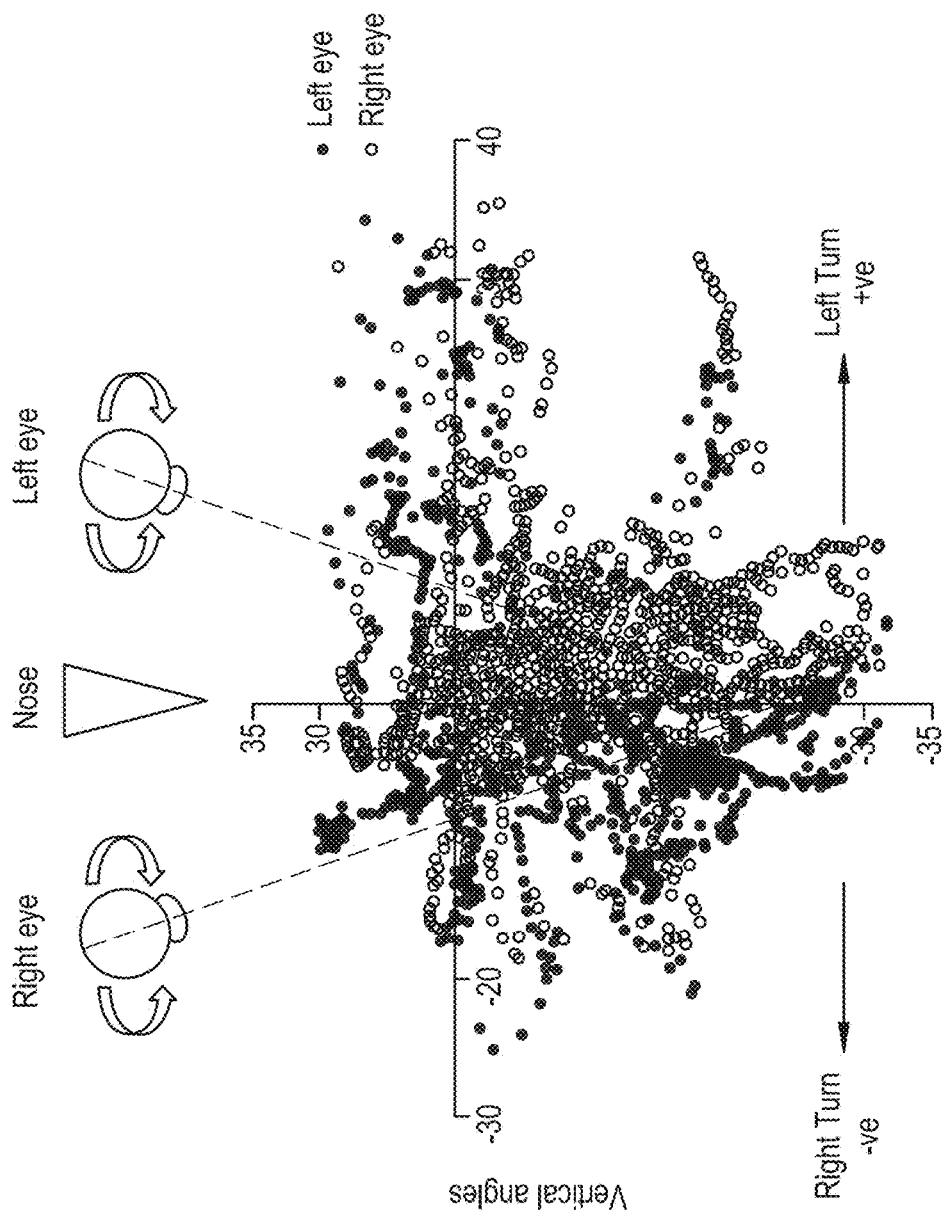

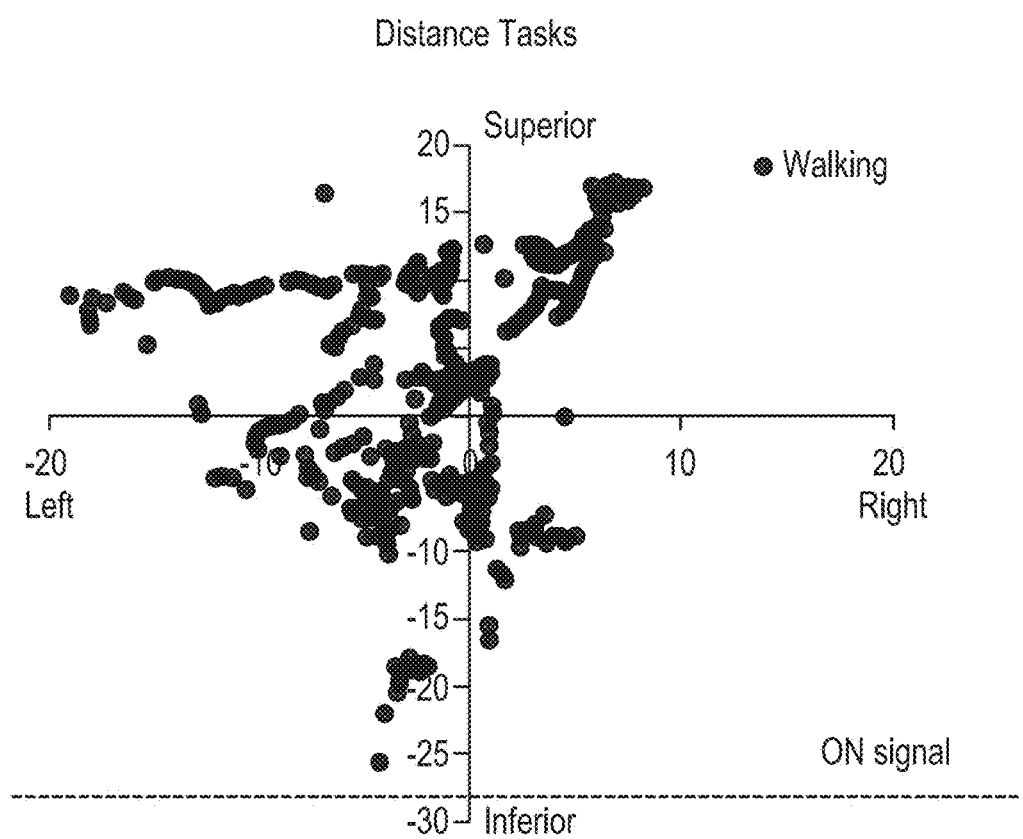

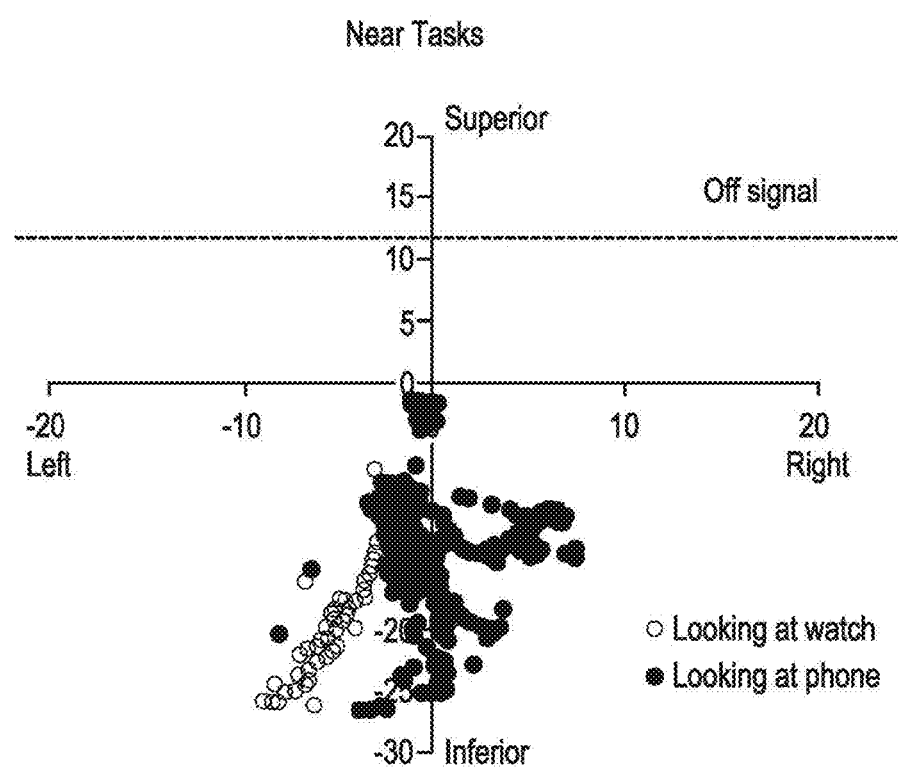

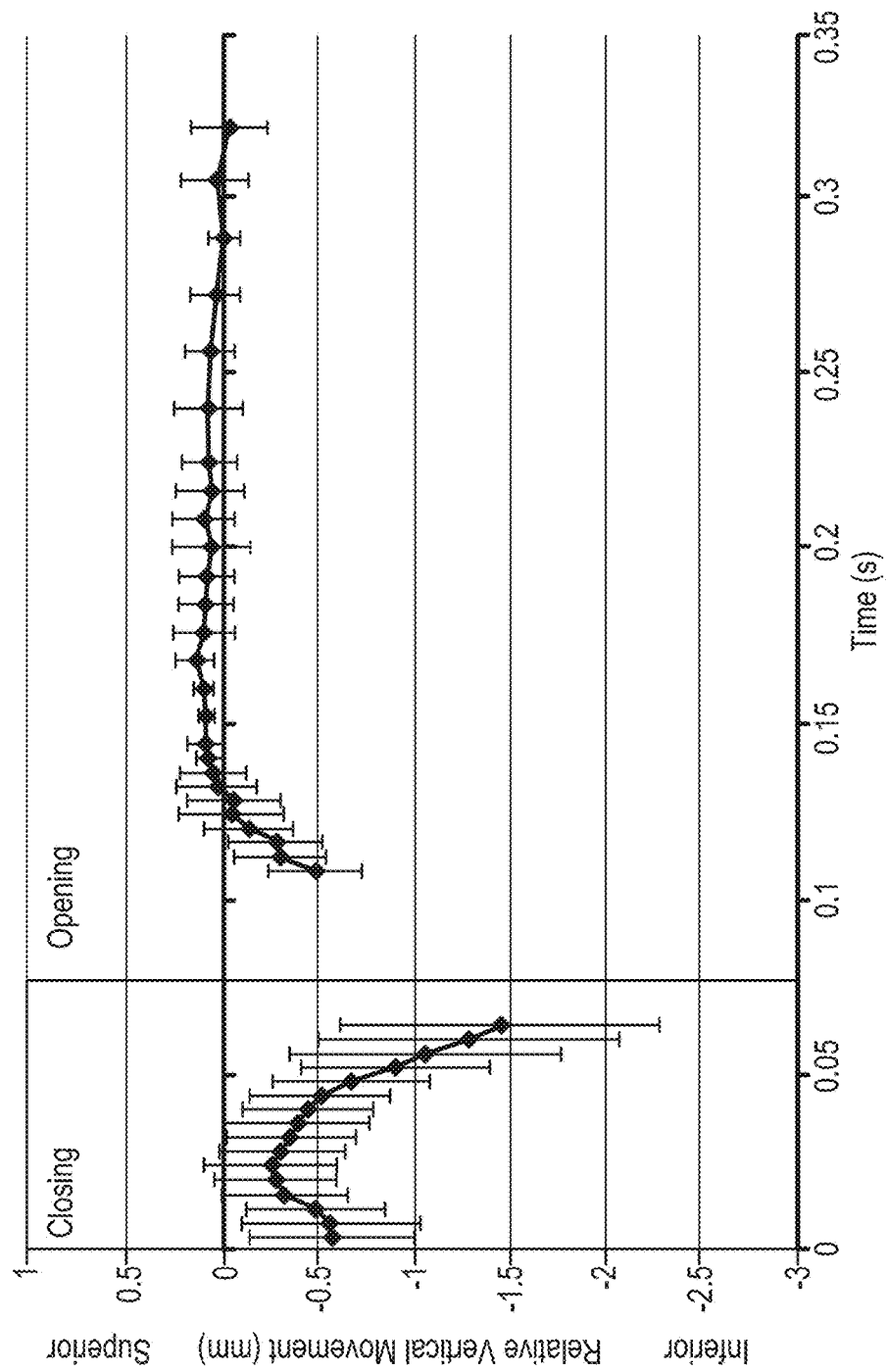

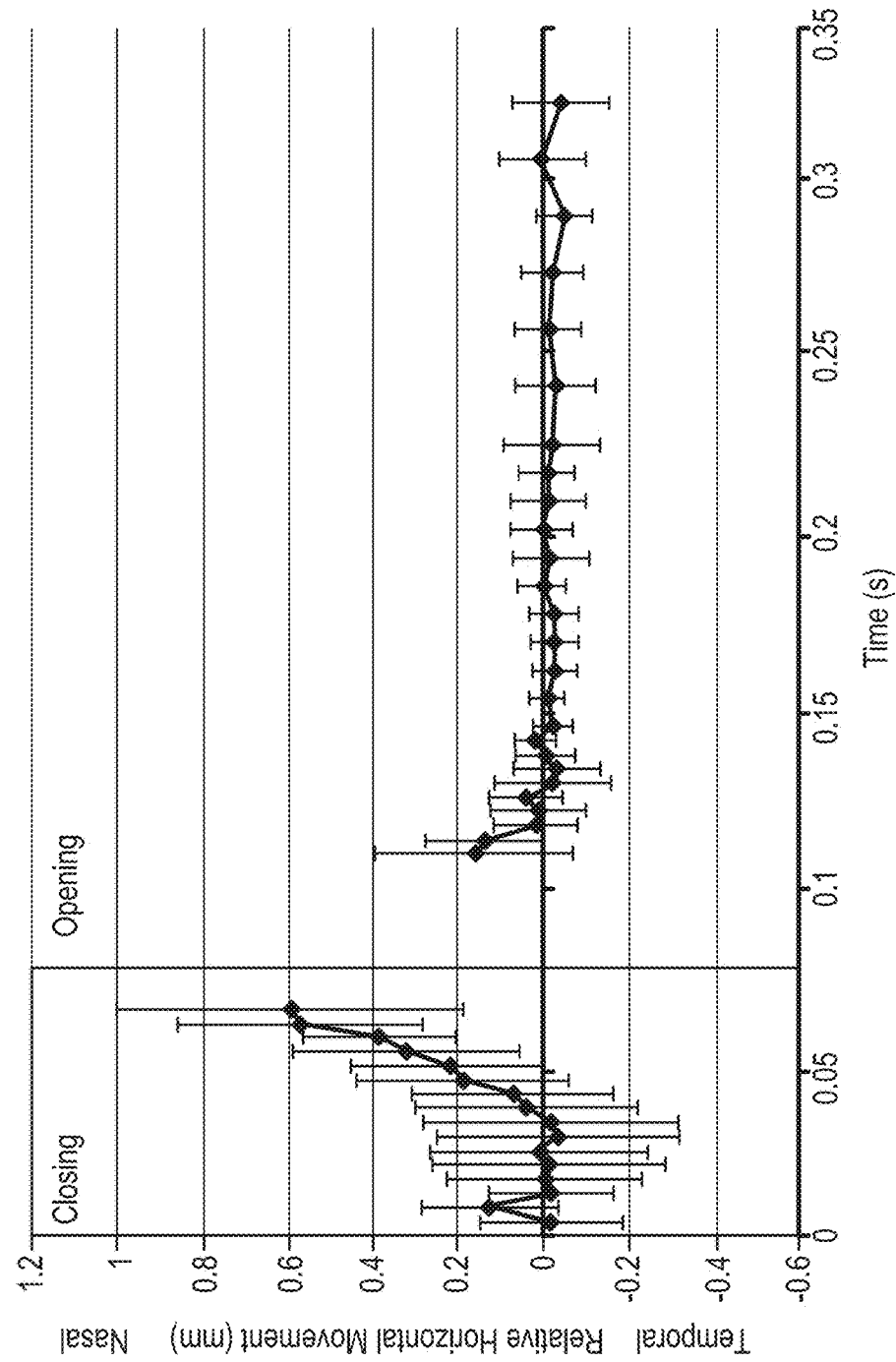

ELECTRONIC OPHTHALMIC DEVICE WITH EXTREME GAZE ANGLE DETECTION

BACKGROUND OF THE INVENTION

1. Field of the Invention

The present invention relates to powered or electronic ophthalmic devices, and more particularly to a powered or electronic ophthalmic device having the ability to monitor and sense extreme gaze angle and use this information to control the focal state of the lens of the device as well as for control of, or input to, other device parameters.

2. Discussion of the Related Art

Powered or electronic ophthalmic devices or lenses can enable a variety of uses not possible with conventional static lenses. Ophthalmic lenses may include spectacle lenses, intraocular lenses, contact lenses, or even corneal onlays or inlays, for use both on and within the eye. These lenses may incorporate a lens assembly having an electronically adjustable focus mechanism to augment or enhance performance of the eye. Lenses, such as contact lenses and intraocular lenses, are currently utilized to correct vision defects such as myopia (nearsightedness), hyperopia (farsightedness), presbyopia and astigmatism. However, properly designed lenses incorporating additional components, specifically powered components, may be utilized to enhance vision as well as to correct vision defects.

Contact lenses have been utilized commercially to improve vision since the 1950s. Early contact lenses were made or fabricated from hard materials, and were relatively expensive and fragile. In addition, these early contact lenses were fabricated from materials that did not allow sufficient oxygen transmission through the contact lens to the conjunctiva and cornea, which potentially could cause a number of adverse clinical effects. Although these contact lenses are still utilized, they are not suitable for all patients due to their poor initial comfort.

Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. Prior to the incorporation of electronics into contact lenses, as disclosed in U.S. Pat. No. 4,702,573, an early attempt to address the diminished far and near vision capacity of a presbyopic patient utilized the downward gaze of a patient and the interaction of the lens surface with the lower eyelid. The '573 patent relied on the downward gaze of the wearer and the resulting movement of the lens to interact with the lower eyelid producing a thickened bulge in the optical zone. This resulted in a change in power of the lens due to the thickness change. Thus variable power in the lens could be achieved depending on how much thickness change occurred as a result of the lens interacting with the lower eyelid when the wearer gazed downward. Because downward gaze is typically associated with near vision needs, this solution can be a viable one to enable a power change to the lens at the time it is needed; however, there may be additional instances when a power change is required that is not associated solely with downward gaze.

To achieve enhanced functionality, recent activity has focused on electronic or powered lenses which incorporate various circuits and components that are integrated into these polymeric structures. See U.S. Pat. Nos. 9,050,185; 8,967,488; 8,857,983; 8,080,187; 7,931,832; amongst others, each of the specified above patents are hereby incorporated by reference. For example, these include control circuits, microprocessors, communication devices, power supplies, sensors, actuators, light-emitting diodes, and miniature antennas may all be integrated into contact lenses via custom-built optoelectronic components to not only correct vision, but to enhance vision as well as provide additional functionality as is explained below. Electronic and/or powered ophthalmic lenses may also be designed to provide enhanced vision via zoom-in and zoom-out capabilities. See U.S. Pat. Nos. 9,268,155; 9,180,636; 9,158,127; 8,906,088; 8,767,308; 8,665,526; and 8,348,424; each of which is hereby incorporated by reference. With the ability to zoom-in and zoom-out one will also require when and how this function should be activated. See both U.S. Pat. Nos. 9,351,827; and 8,092,013, which are hereby incorporated by reference. Control of an electronic or a powered ophthalmic lens may be accomplished through a manually operated external device that communicates with the lens, such as a hand-held remote unit, a smart phone or smart watch, a lens storage container, or lens cleaning box. For example, a fob may wirelessly communicate with the powered lens based upon manual input from the wearer. Alternately, in accordance with the present invention, control of the powered ophthalmic lens may be accomplished via feedback or control signals directly from the wearer.

In addition, sensors built into the lenses may be utilized to detect light incident on the eye to compensate for ambient light conditions or for use in determining blink patterns. See U.S. Pat. No. 9,072,465, which is hereby incorporated by reference. The proper combination of devices could provide significantly enhanced functionality; however, there are a number of difficulties associated with the incorporation of extra components on a piece of optical-grade polymer having a thickness on the order of a piece of plastic/Saran™ wrap. In general, it is difficult to manufacture such components directly on the lens for a number of reasons, as well as mounting and interconnecting planar devices on a non-planar surface. It is also difficult to manufacture to this scale. The components to be placed on or in the lens need to be miniaturized and integrated onto just 1.5 square centimeters of a transparent polymer of minimal thickness while also protecting the components from the liquid environment on the eye. It is also potentially difficult to make a contact lens comfortable and safe for the wearer due to the added thickness of additional components as well as the impact of the material choices of the components.

U.S. Pat. No. 6,851,805, discloses the use of a view detector attached to an electro-active contact lens system which, according to the disclosure, may be used to automatically determine where the wearer is looking, and thus activate the electro-active element to provide the proper focal length based on the gaze of the wearer. Further discussion in the '805 patent indicates the view detector may be a range finder or an eye tracker such as a micro-gyroscope, micro-accelerometer or tilt switch, or a combination of one or more of these items. The '805 patent discusses the use of a mercury tilt switch to determine whether the wearer's eyes are tilted down or up at a given angle above or below that which would be indicative of someone looking straight ahead into the distance. Other than the mercury tilt switch, no other embodiments are described, nor are any designated angles at which to activate the switch specified in this disclosure. The only mention is that the angle is different from that of looking straight ahead. One must also be cognizant about the biocompatibility requirements of the materials and components of the powered lens due to their potential or likely contact with tissue, either through normal use or unintended degradation of the seals/encapsulation while the device is being worn. Additionally there are area and volume constraints of an ophthalmic device that must also be considered. Given the minimal area and volume for an item such as a contact lens, and the environment in which it is to be utilized, the physical realization of the device must overcome a number of problems, including mounting and interconnecting a number of electronic components on a non-planar surface, the bulk of which comprises optical-grade plastic. Accordingly, there exists a need for providing a biocompatible, mechanically and electrically robust electronic contact lens.

Furthermore, powered or electronic ophthalmic lenses may have to account for certain unique physiological functions from the individual utilizing the powered or electronic ophthalmic lens. More specifically, powered lenses may have to account for blinking, including the number of blinks in a given time period, the duration of a blink, the time between blinks and any number of possible blink patterns, for example, if the individual is dozing off. Blink detection may also be utilized to provide certain functionality, for example, blinking may be utilized as a means to control one or more aspects of a powered ophthalmic lens. In U.S. Pat. No. 9,442,310 use of a capacitive sensor coupled with gaze detection circuitry and logic are utilized to identify the gaze direction and focal distance. This is achieved by first calibrating the device and identifying different capacitance values which are associated with different gazing directions or focal distances. With the device being worn, the wearer is instructed to first close then open his/her eyelids, then look straight forward, and then look at different focal distances and different directions. During this procedure, the capacitance values from each of these situations is measured and stored. Thus in practice the capacitance value returned during use can then be compared and matched to one of the pre-determined calibration values from each of the use cases tested, which can then infer the likely gaze direction by associating it to the pre-determined value. This comparison/result is dependent on both the number of conditions tested during the calibration mode as well as the accuracy of the determination itself, and may change over the course of a day as the eye tires and the physical relationships between the contact lenses and the cornea and lid change, thus potentially requiring recalibration at times. Additionally, external factors, such as changes in light intensity levels, and the amount of visible light that a person's eyelid blocks out, have to be accounted for to determine if any differences exist with current conditions as compared to the conditions when the device was calibrated.

Accounting for contact lens movement due to blinking is another consideration. Furthermore, unintentional eye movement for purposes other than vision, for example, facial expressions or head rolling, may contribute to false positive readings. Accordingly, as it relates to the capacitive sensor approach, there exists a need for a means and method for detecting certain physiological functions, such as a length of eye closure or a blink or when additional focal power is required. The sensor being utilized needs to be sized and configured for use in a contact lens. In addition there exists a need to detect the position of a user's eyelids. An eyelid position sensor could be used to determine if a user is falling asleep, for example, to log a data event of the wearer falling asleep. There are existing systems for detecting lid position; however, they are limited to devices like camera imagers, image recognition, and infrared emitter/detector pairs, which rely on reflection off the eye and eyelid. Existing systems to detect lid position also rely on the use of spectacles or clinical environments and are not easily contained within the space afforded by a contact lens. In US Published Patent Application US2014/0243971, assigned to Applicant and hereby incorporated by reference, an electronic ophthalmic lens with an eye gaze sensor to detect and track pupil position may be used to control various aspects of the ophthalmic lens. This includes items such as changing the focus of the lens for a presbyopic wearer, which is described in this published patent application. Furthermore, as discussed in US Published Patent Application 2014/0243971, there exists a correlation between pupil convergence and focusing on near objects. Physiologically, when an individual focuses on a near object, the pupils move downwardly and inwardly towards the nose. Thus sensing of pupil convergence is yet another possible item to be used to signal the need to trigger an action of the powered lens such as changing the power when the lens wearer's pupils converge. The measurement of convergence requires measuring small angles and differentiating even smaller changes to these values.

Lastly, because of the complexity of the functionality associated with a powered lens, the high level of interaction between all of the components comprising a powered lens, a multitude of use cases, and differences in anatomy of the eye from one wearer to another, there is a need to coordinate and control the overall operation of the electronics and optics comprising a powered ophthalmic lens as well as taking into account its interaction with the eye itself. Moreover, while blink detection, eye gaze tracking, and pupil convergence may be viable methods to control powered lenses one would also have to account for and devise a way to ascertain if the occurrence of one or more of these events should indeed trigger an event. Specifically, each of these eye actions could occur in other situations where there was no need to trigger an event impacting the powered lens, or worse where the triggering of a change may result in potential harm, for example, power change to the lens during highway driving. Accordingly, there is both a need for a system to control the operation of all of the other components that is safe, low-cost, and reliable. The system should also have a low rate of power consumption, be scalable for incorporation into an ophthalmic lens, and have a method of triggering distinguishable from ordinary naturally occurring events such as blinking, gazing, and pupil convergence so that the intended effect is both natural and easy to accomplish, yet purposeful to achieve a desired effect.

SUMMARY OF THE INVENTION

In accordance with the present invention, extreme gaze angles, determined by detecting eye positions that exceed normal gaze angles, may be utilized to trigger the change of state of a powered or electronic ophthalmic device or other suitable control function. The direction of gaze may be determined by any number of suitable devices, for example, with iris-facing photodetectors best used with spectacles to observe the pupils, eye gaze sensors or accelerometers to track/measure vertical gaze positions (ie: eye angles+head angles) or with capacitive or light-based sensors to monitor the position of the eyes relative to the eyelids. Extreme gaze angles could be a learned trigger, for example, looking down to focus near and up to focus far. They can also be combined with other purposeful eye movements to provide a host of distinct sequences discernable by the powered lens to trigger multiple actions based on the sequence provided.

Convergence has already been discussed as an activation method, but it relies on measuring approximately a 4-degree angle and then differentiating small changes in angle to detect convergence and the desire to focus up-close. In accordance with the present invention, extreme vertical gaze angle detection may be much more reliable and faster than detecting convergence due to a greater difference of the angular magnitudes. For example measuring large angle movements above or below certain thresholds such as −27 and +12 degrees relative to horizontal in accordance with the present invention should be easier to accomplish than assessing smaller dimensional or angular changes. Extreme gaze angle may be more natural, easier, and more acceptable than blink control alone, although blink control may be used in combination with gaze angle in accordance with the present invention. Applicants have researched and determined what are believed to be acceptable ranges of both upward and downward extreme gaze angles which are not only measurably distinguishable from gaze angles associated with everyday activities, but which do not occur naturally. Furthermore it is important that while satisfying the former it is also critical to ensure these gaze angles are still achievable by the wearer on purpose and still within human eye movement capability.

Even if other natural/biologically occurring activation methods (such as convergence and ciliary muscle detection) are used to activate power changes, extreme gaze angles may be utilized to augment these more natural activation methods and may be particularly useful during calibration procedures and customization, for example, to accept/reject settings, change modes, or change values. This could act very much like the up/down/left/right cross on a remote control, with up/down used to increment/decrement a parameter and left/right used to toggle through parameters, but rather than using one's finger on the various buttons one simply artificially gazes in the relevant direction in an extreme fashion in accordance with the present invention. Some potential parameters may include focus distance threshold, distance hysteresis, activation time, and other control parameters. It is important to note that utilizing extreme gaze for this purpose requires an action to be taken in a physiologically acceptable time frame. Thus measuring the time or duration of the action and ensuring that the action is completed within a set time period is another way to distinguish that the action is indeed purposeful. In an alternative embodiment, combining purposeful extreme gaze angle movements with blinks for instance significantly increases the number of available input sequences to the lens. Simply stated, the extreme gaze and its detection should preferably be done in a period of time that does not interfere with other actions. In accordance with the present invention, applicants have determined that this period of time should typically not be greater than several hundred milli-seconds, specifically a period of 500 miliseconds or less is preferred in accordance with the present invention.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 6 shows a plot of eye movement during periods of convergence.

FIG. 7 shows a scatter plot of both the horizontal and vertical angles of both the left and right eye positions during normal gaze.

FIG. 8B is a scatter plot showing typical gaze angles which occur during the activity of walking and also indicating the lower limit of gaze angle during this particular task in accordance with the present invention.

FIG. 8C is a scatter plot showing typical gaze angles which occur during the activity of looking at one's watch, or looking at one's phone and also indicating the upper limit of gaze angle during this particular task in accordance with the present invention.

FIG. 9A shows a plot of the average of vertical lens movement during a blink of six human subjects.

FIG. 9B shows a plot of the average of horizontal lens movement during a blink of six human subjects.

DETAILED DESCRIPTION OF THE PREFERRED EMBODIMENTS

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, light-emitting diodes, and miniature antennas may all be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses.

The powered or electronic contact lens of at least one exemplary embodiment includes the necessary elements to monitor the wearer with or without elements to correct and/or enhance the vision of patients with one or more of the above described vision defects or otherwise perform a useful ophthalmic function. The electronic contact lens may have a variable-focus optic lens, an assembled front optic embedded into a contact lens or just simply embedding electronics without a lens for any suitable functionality. The electronic lens of the present invention may be incorporated into any number of contact lenses as described above. In addition, intraocular lenses (IOL's) may also incorporate the various components and functionality described herein. There would be differences between contact lenses and IOL's that would have to be addressed to ensure similar performance. Items such as resolution of some of the measurements may have to be increased given there would be less absolute movement with an IOL as compared to an contact lens. Relative measurements to the eyelid would also have to be adjusted since the placement of an IOL relative to the eyelid would be different as compared to a contact lens which is essentially adjacent to the eyelid. While both contact lenses and IOL's could incorporate the various components and functionality, for ease of explanation, the disclosure will focus on an electronic contact lens intended for single-use daily disposability.

Figure 1:
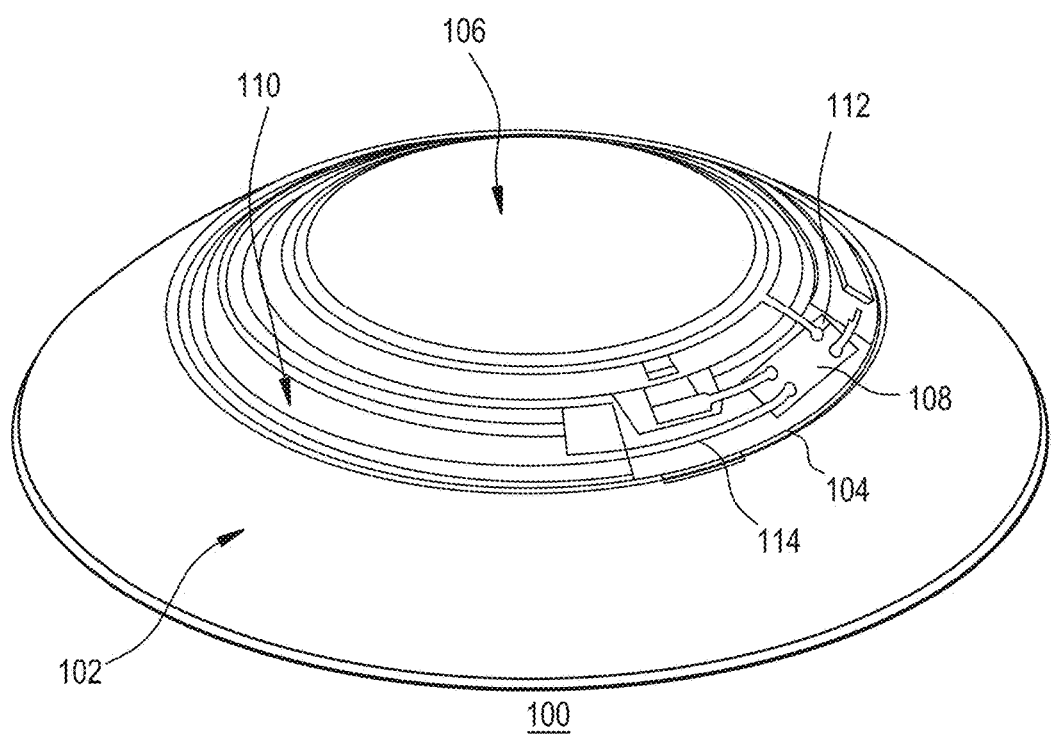
FIG. 1 is a diagrammatic representation of an exemplary contact lens with an electronic insert comprising a gaze angle detection system in accordance with the present invention.

The present invention may be employed in a powered ophthalmic lens or powered contact lens having an electronic system as shown in FIG. 1, which actuates a variable-focus optic or any other device or devices configured to implement any number of numerous functions that may be performed. FIG. 1, illustrates an exemplary contact lens 100 with an electronic insert having a gaze angle detection system in accordance with the present invention, Lens 100 comprises a soft plastic portion 102 which includes electronic insert 104. The electronic insert 104 is comprised of a lens 106 which is activated by the electronics including an integrated circuit 108 and a gaze angle sensor 112. The electronic system includes one or more batteries 110 or other suitable power sources, and the components are preferably connected by wiring traces 114. The battery or power source 110, supplies power for numerous components in the system. The power may be supplied from a battery, energy harvester, photovoltaics or other suitable means as is known to one of ordinary skill in the art. Essentially, any type of power source 110 may be utilized to provide reliable power for all of the electrical components of the system. The electronic system may also include power management circuitry, one or more sensors, clock generation circuitry, control algorithms and circuitry, and lens driver circuitry. The complexity of these components may vary depending on the required or desired functionality of the lens. Alternatively, the contact lens may just monitor the wearer in at least one embodiment. In an alternative exemplary embodiment, communication functionality is provided by an energy harvester that acts as the receiver for the time signal, for example in an alternative embodiment, the energy harvester is a solar cell or a radio frequency (RF) receiver, which receives both power and a time-base signal (or indication). Gaze angle sensors may comprise any suitable device, for example, an iris-facing photodetectors to observe the pupils or alternatively accelerometers to track the movement of the eyes in accordance with the present invention. One may also utilize sensors to monitor one or more of the six extra-ocular muscles that control eye movement as these extra ocular muscles all are attached to the globe of the eye. These six extra-ocular muscles include: the superior rectus whose primary function is elevation, intorsion and adduction; the lateral rectus, whose primary function is abduction; the inferior rectus, whose primary function is depression, extorsion and adduction; the medial rectus, whose primary function is adduction; the superior oblique, whose primary function is intorsion, depression and abduction; and the inferior oblique whose primary function is extorsion, elevation and abduction.

Figure 2A:
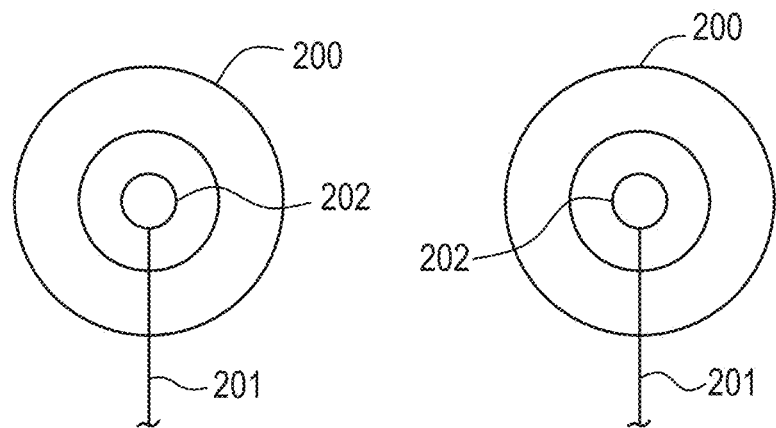
FIG. 2A is a diagrammatic, front perspective representation of the eyes of an individual gazing at a distant object.
Figure 2B:
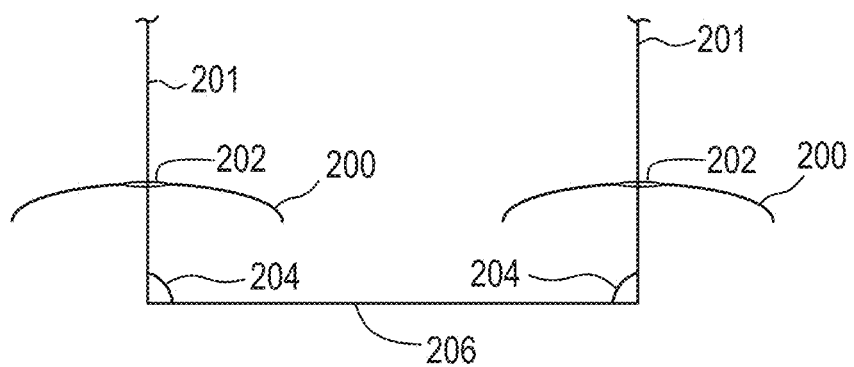
FIG. 2B is a diagrammatic, top perspective representation of the eyes of FIG. 2A

Eye tracking is the process of determining where an individual is looking; this includes both point of gaze and motion of the eye relative to the head as well. FIGS. 2A and 2B show both an idealized front view and top view of two eyes 200 of an individual who is looking at a distant object. When looking at a distant object such as when one is driving a car, or walking, the eyes 200 are focused on objects in the distance (i.e. far focus). In far focus, the pupils 202 are centered and typically will track together for normal healthy eyes (no muscular or neurological problems). That is to say, lines of sight 201 from the pupils 202 to the object (not shown) will be parallel. This is also indicated by angles 204 both being equal to ninety (90) degrees relative to the coronal or frontal plane of the head 206. When viewing objects in the distance, even with objects in motion, as the eyes 200 and corresponding pupils 202 track the object as it moves, the angles 204 will remain close to ninety (90) degrees, due to the distance between the eyes 200 being so much less as compared to the distance from the eyes 200 to the object (not shown).

Figure 3A:
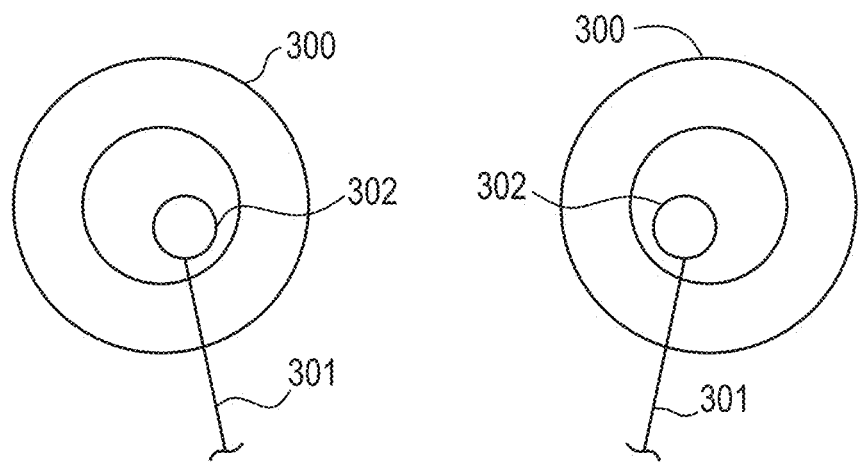
FIG. 3A is a diagrammatic, front perspective representation of the eyes of an individual gazing at a near object.
Figure 3B:
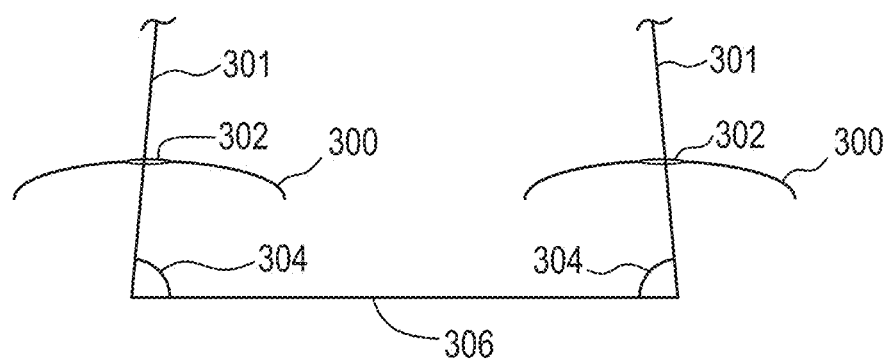
FIG. 3B is a diagrammatic, top perspective representation of the eyes of FIG. 3A

When viewing an object up close or very near to the eyes, such as reading a book, or looking at your watch, we have a different situation as shown in FIGS. 3A and 3B. In this situation, the pupils 302 of eyes 300 converge, (i.e. they are no longer parallel but rather have a nasal and slightly inferior bias) in order to observe and focus on the object which is now much closer (i.e. near focus). Lines of sight 301 are no longer parallel, and angles 304 are now less than ninety (90) degrees relative to the coronal or frontal plane of the head 306. In addition, although not shown, the lines of sight 301 are also tilted slightly downward or inferior relative to a horizontal or transverse plane of the head.

Figure 4A:
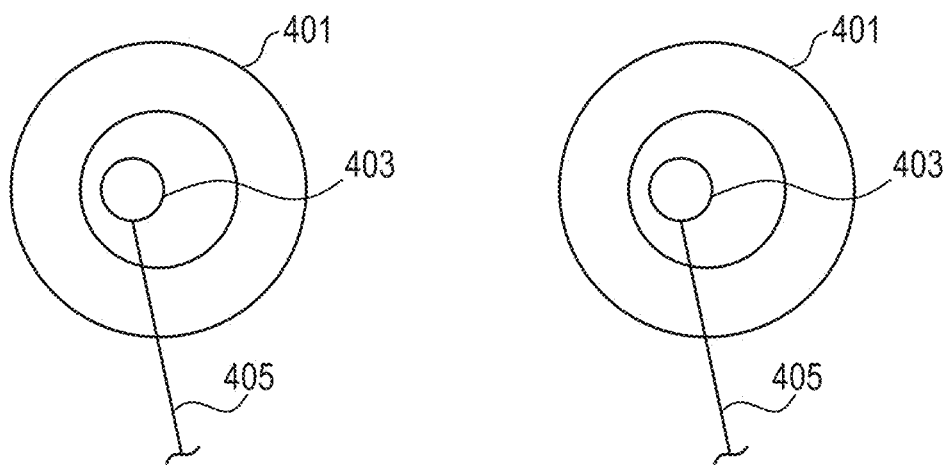
FIG. 4A is a diagrammatic, front perspective representation of the eyes of an individual gazing to the right.
Figure 4B:
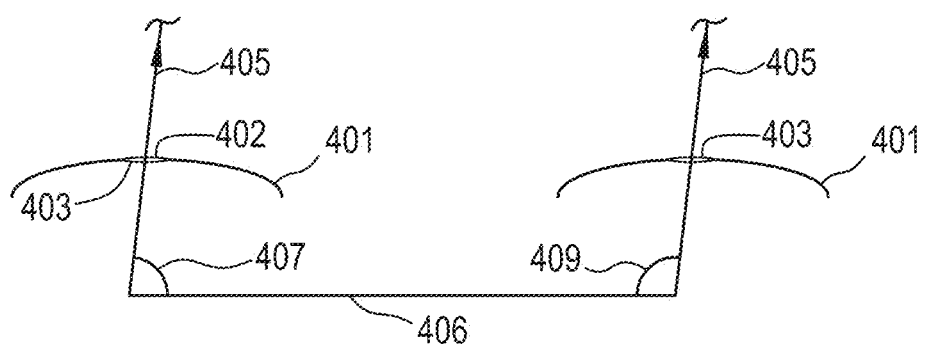
FIG. 4B is a diagrammatic, top perspective representation of the eyes of FIG. 4A

FIGS. 4A and 4B which are similar to both FIGS. 2A and 2B, as well as FIGS. 3A and 3B show eyes 401 and pupils 403 as well as the lines of sight 405 when the viewer is looking at an object (not shown) to the side (in this case the right side). While the lines of sight 405 are still parallel, the angles 407 and 409 are no longer 90 degrees relative to the coronal or frontal plane 406 of the head. But rather angle 407 is less than 90 degrees, while angle 409 is greater than 90 degrees. These angles may be used to determine gaze position. Although the position to the right is used in this example, it should be appreciated that any suitable visible position of the object such as to the left, or downward, or upward, or any combination thereof could be used. Wherever the object appears in the visible three dimensional spaces, a corresponding measurement of the gaze angles could be determined.

Figure 5:
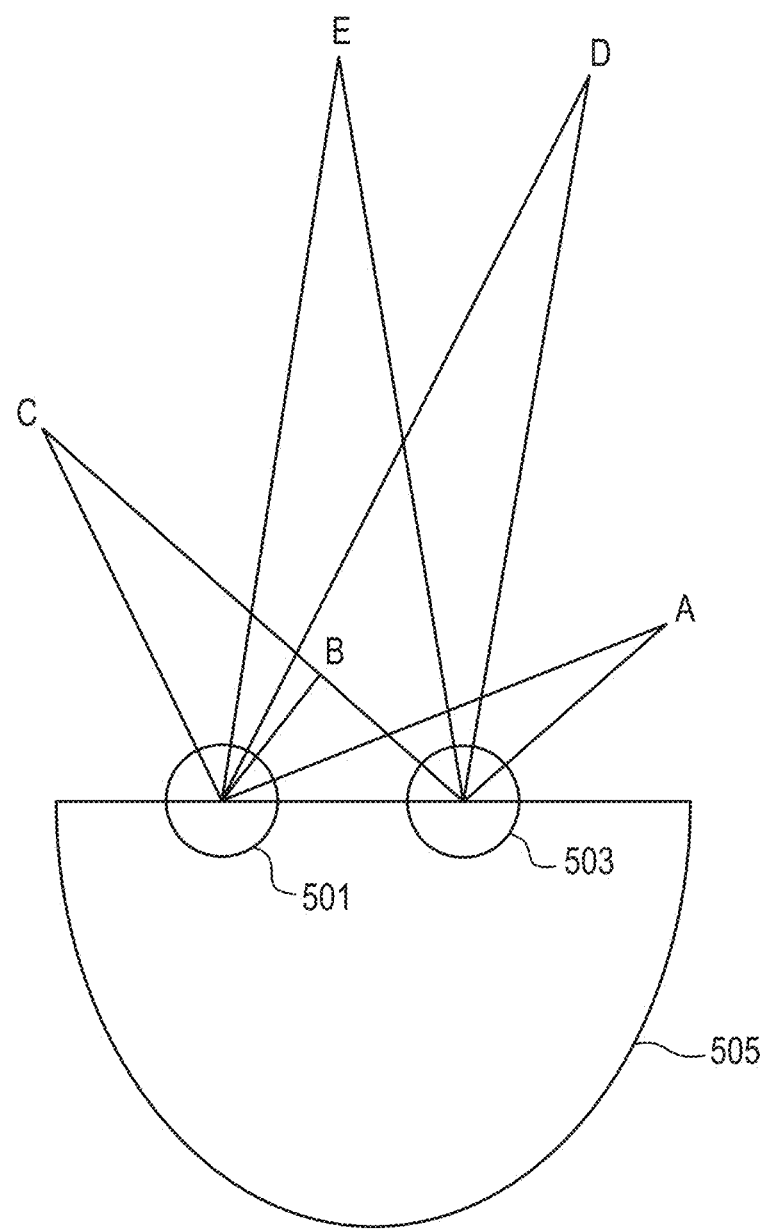
FIG. 5 is a diagrammatic representation of the geometry associated with various gaze directions/angles in two dimensions in accordance with the present invention.

As shown in FIG. 5, the gaze direction or angle is a result of both the orientation of the eyes 501 and 503 relative to the head 505 as well as the orientation of the head 505 itself. While the orientation of the head determines the overall direction of gaze and available field of view which is typically between 150 and 170 degrees relative to one's position, the orientation of the individual's eyes is largely independent of head position and determines the exact gaze direction. Applicants have discovered that the total gaze angles (eye pitch+head pitch) during natural near tasks can be different to the total gaze angles during natural distance tasks. In accordance with the present invention an accelerometer can be used to measure the vertical gaze angle in order to detect the intent of the eye to perform these tasks.

It is important to note, that eye tracking in accordance with the present invention may be set up for gross or fine tracking monitoring. Eyes 501 and 503 can gaze upon various targets labeled A through E in FIG. 5. By connecting the line of sight from each eye to the representative target, and connecting the eyes to each other, a triangle is formed. As FIG. 5 shows, the various included angles for each of the five triangles formed will be dependent on the position of the object. These angles may be measured directly by a sensor system, or determined indirectly from sensor measurements.

Eye gaze direction may be utilized as a direct input into a controller or processing unit to control an action in accordance with the present invention; however, an important and critical issue to address is how to discern the difference between the gaze angle associated with simply gazing at an object because one wants to view the object, with that of a gaze direction/angle that just so happens coincides with the gaze angle when viewing the object. To determine this, applicants researched gaze angles of human subjects during various tasks such as walking both indoors and outdoors, looking at a watch or looking at one's phone. Presbyopes were chosen as subjects since they would receive the most benefit from a lens which had the ability to change focus on demand due to their loss of accommodative abilities. A Tobii eye tracker was worn by a group of presbyopes while doing normal daily activities including both far and near tasks. Visual tasks included activities such as walking indoors and outdoors, looking at ones watch, doing computer work and checking on e-mails on one's hand-held device. These tasks were performed with a natural gaze and head orientation. As shown in FIG. 6, during periods of convergence when the subject has focused their eyes on a point of interest, both right and left eye positions/gaze angles while different from eye to eye, do remain fairly consistent while the object is in focus. One can also note the extent of variability of, or noise in eye position between these events when the eyes are not necessarily fixated on a particular point in space. Having an improved understanding of both these situations is vital if one wants to use eye gaze angles as a proxy for commands to control functions in a powered or electronic ophthalmic device in accordance with the present invention. It is possible that a particular gaze angle could occur during either periods of focusing on objects, or when the eye is relaxed and saccades (involuntary, abrupt, small movements of both eyes when changes in eye fixation occur) occur, and could result in a false positive or negative readings. As shown in FIG. 7, a scatter plot can be created showing the numerous angles (both horizontally and vertically) of both eye positions. This information can then be used to identify unique gaze angle/positions that are anatomically achievable but do not occur under normal activities.

Figure 8A:
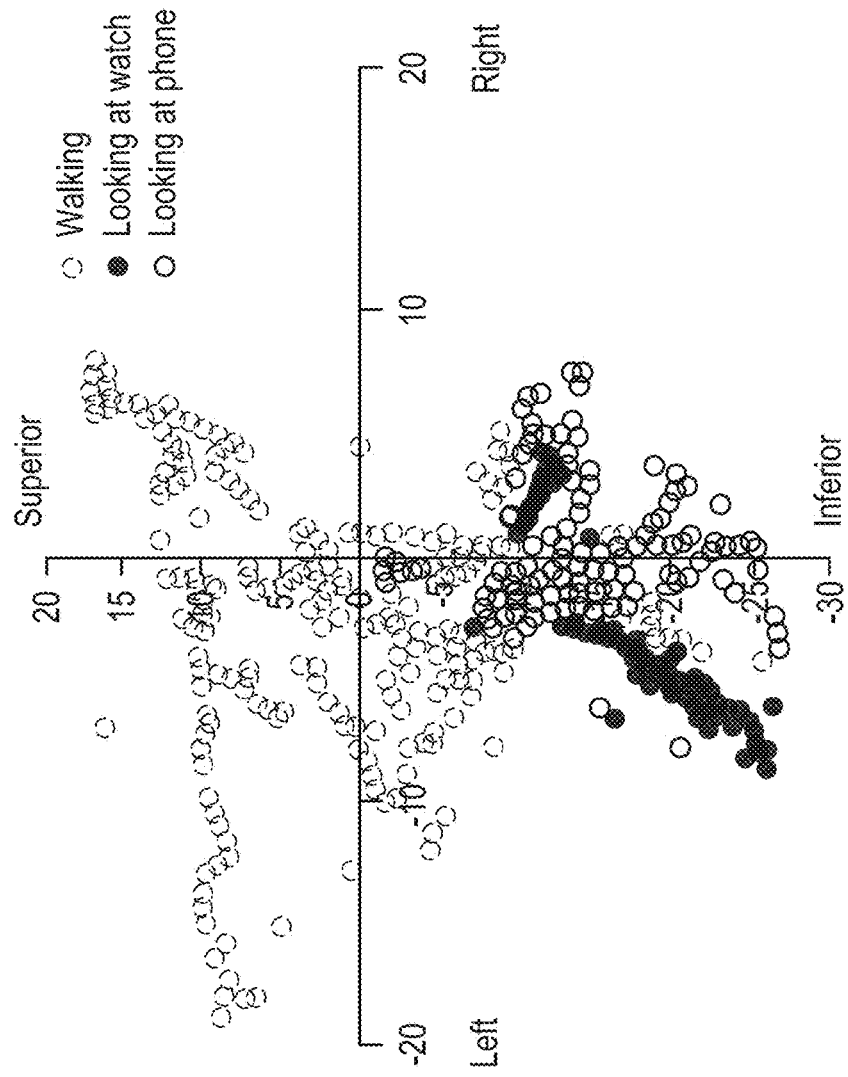
FIG. 8A is a scatter plot showing actual horizontal and vertical gaze angle measurements from a human subject during typical activities such as walking, looking at one's watch, or looking at one's phone.

FIG. 8A shows these unique gaze angles for a subset of individuals during various activities (walking, looking at one's watch, looking at one's phone) and when one makes the distinction between both near and far tasks, and replots the data separately as in shown in FIGS. 8B and 8C, one can see the grouping of gaze angle/positions for both far (FIG. 8B) and near (FIG. 8C) activities. As these plots show, there are distinct groupings of gaze angles between these far and near activities. Based on this clinical finding, one can define a level or threshold value as to when to turn on and when to turn off a particular function, (ie: a triggering event). By selecting a level/gaze angle below which no points are located for the various gaze angles encountered during walking, a distance task, but are still within the anatomically acceptable limits, one may avoid any false positive signals as shown in FIG. 8B. In this case applicants research indicates this level or triggering event to be somewhere between negative 25 and 30 degrees from horizontal and preferably negative 27 degrees from horizontal in accordance with the present invention. Designating this as an "on signal" as shown in FIG. 8B, and having the wearer intentionally move their eyes downward an extreme amount would trigger the "on signal" as the downward gaze of the eye passes the previously designated threshold value. Similarly as shown in FIG. 8C, one can define a level or threshold value as to when to turn off a particular function. By selecting a level/gaze angle above which no points are located for the various gaze angles encountered during looking at one watch, or one's phone (near tasks), but are still within the anatomically acceptable limits, we can avoid any false positive signals as shown in FIG. 8C. In this case applicants research indicates this level or the triggering event to be somewhere between positive 10 to 15 degrees from horizontal and preferably positive 12 degrees from horizontal in accordance with the present invention. Designating this as the "off signal" as shown in FIG. 8C, and having the wearer intentionally move their eyes upward an extreme amount would trigger the "off signal" as the upward gaze of the eye passes the previously designated threshold value, returning the lenses to their default setting. Table 1 below summarizes the mean angle and upper and lower limits of vertical gaze that was determined based upon a second more comprehensive study of 50 presbyopic subjects for both Distance and Near Tasks within 95% probability limits.

TABLE 1

| Distance Tasks (Average of 50 Presbyopes - 95% Confidence limits) | |
|---|---|
| Mean Angle | −6.364 degrees |
| Lower Limit | 2.112 degrees |
| Upper Limit | −14.440 degrees |
| Near Tasks (Average of 50 Presbyopes - 95% Confidence limits) | |
| Mean Angle | −15.388 degrees |
| Lower Limit | −2.810 degrees |
| Upper Limit | −27.966 degrees |

Figure 8D:
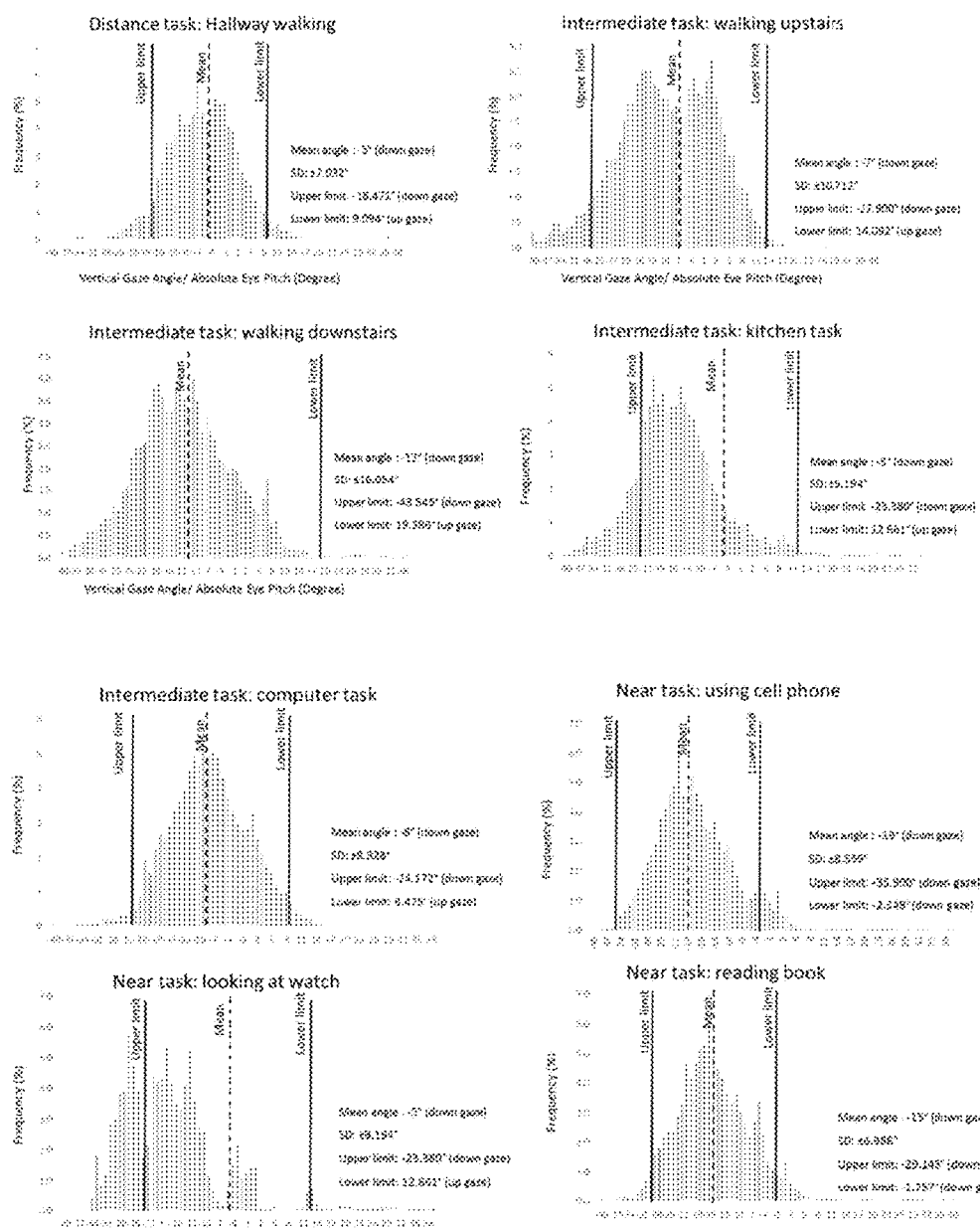
FIG. 8D shows a set of eight plots for eye pitch (ie: vertical gaze angle) for distinct events encompassing distance, intermediate and near tasks.

As shown in FIG. 8D, this additional investigation in which a group of fifty (50) presbyopes performing more diverse tasks including intermediate tasks as well as distance and near tasks confirmed and further supported distinct distributions of absolute eye pitch (ie: vertical gaze angle) during these individual events. Also shown for each of the eight plots is the mean angle for each condition as well as the upper and lower limits of the gaze angles for each condition within 95% confidence limits.

In a preferred embodiment of the present invention, there can exist two states, the default or unpowered state and an activated or powered state. The "on signal" turned on by looking downward an extreme amount, could be used to activate the focal power of the lens to focus on near items. Likewise, looking upward an extreme amount could be used to turn off, or return the system to its default setting allowing the lens to focus on far/distance items in accordance with the present invention. Activating the power change in this fashion should be more natural and acceptable to the wearer than requiring a series of blinks or following a complicated and extensive calibration procedure. It is also much simpler and likely quicker than relying on complicated circuitry and sensors to measure the conditions related to convergence or ciliary muscle action to assess when the need for a focal power change is likely required. With respect to eye-blinking, it is also important to understand the interaction of the blinking of the eyelids and the resulting lens movement after a blink. FIGS. 9A and 9B, respectively show the relative vertical and horizontal movement of the lens upon the eyelid closing and then opening over time, as the plots show, the lens can move significantly but does reposition itself to its starting position upon the eyelid opening. While most if not all contact lenses will move on eye, depending on lens geometry and material utilized these movements while overall will be somewhat similar on the macro scale, will also differ from lens design to lens design on a finer micro scale. By incorporating a blink detection sensor in conjunction with the eye gaze sensor, one can significantly increase the number of input sequences to trigger different functional aspects of the powered lens. Table 2 below shows some selected input sequences using only downward or upward gaze with blinking twice between the gazes.

TABLE 2

|  | 1st Event | 2nd event | 3rd event | 4th event |
|---|---|---|---|---|
| Input Sequence #1 | Extreme downward gaze | | | |
| Input Sequence #2 | Extreme downward gaze | Extreme upward gaze | | |
| Input Sequence #3 | Extreme downward gaze | Extreme upward gaze | Extreme downward gaze | |
| Input Sequence #4 | Extreme downward gaze | Blink 2x | Extreme upward gaze | |
| Input Sequence #5 | Extreme downward gaze | Extreme upward gaze | Extreme downward gaze | Extreme upward gaze |
| Input Sequence #6 | Extreme downward gaze | Blink 2x | Extreme upward gaze | Extreme downward gaze |
| Input Sequence #7 | Extreme downward gaze | Extreme upward gaze | Blink 2x | Extreme downward gaze |
| Input Sequence #8 | Extreme upward gaze | | | |
| Input Sequence #9 | Extreme upward gaze | Extreme downward gaze | | |
| Input Sequence #10 | Extreme upward gaze | Extreme downward gaze | Extreme upward gaze | |
| Input Sequence #11 | Extreme upward gaze | Blink 2x | Extreme downward gaze | |
| Input Sequence #12 | Extreme upward gaze | Extreme downward gaze | Extreme upward gaze | Extreme downward gaze |
| Input Sequence #13 | Extreme upward gaze | Blink 2x | Extreme downward gaze | Extreme upward gaze |
| Input Sequence #14 | Extreme upward gaze | Extreme downward gaze | Blink 2x | Extreme upward gaze |

The addition of simply blinking twice after the initial and before a subsequent extreme gaze adds additional permutations of sequences which may be realized (see input sequences 4, 6, 7, 11, 13, & 14 in table 2). Increasing the number of blinks or total number of events in the sequence or adding medial and lateral extreme gaze angles further increases the available options. By combining these purposeful movements into a specified sequence that is unlikely to occur naturally, one can avoid false positive signals from that of the triggering of an event, for example, tilting one's head back versus rolling the eyes up). Abrupt intentional movements up and down coupled with timing or specified blink patterns in combination with intentional eye movements/gaze serve to distinguish the triggering event from naturally occurring combinations. If further checking is required, lid movement and muscle sensing can also be utilized to complement the above.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A powered ophthalmic device, the powered ophthalmic device comprising:
   a variable optic lens;
   means for generating power, and
   an extreme gaze angle detection system incorporated into the lens, the extreme gaze angle detection system having a sensor to detect at least one of upper and lower vertical angles of extreme gaze, medial and lateral angles of extreme gaze, a lens actuator, a controller cooperatively associated with the sensor and the actuator, and the controller configured to receive and assess input from the sensor and send output to the actuator to implement a lens function in response to a detection of an extreme gaze angle between negative 25 and negative 30 degrees from horizontal or between 10 to 15 degrees from horizontal.

2. The powered ophthalmic device of claim 1 wherein the sensor is an accelerometer.

3. The powered ophthalmic device of claim 1 wherein the sensor is an eye gaze sensor.

4. The powered ophthalmic device of claim 1 wherein the lens function is a change in focal power.

5. The powered ophthalmic device of claim 1 where the ophthalmic lens further comprises a blink detection sensor.

6. The powered ophthalmic device of claim 5 wherein angles of extreme gaze are used in combination with a specified number of blinks as determined by the blink detection sensor to implement a lens function.

7. The powered ophthalmic device of claim 6 wherein the lens function is a change in focal power.

8. The powered ophthalmic device of claim 6 wherein the input from the sensor is received and assessed within a period of 500 miliseconds or less.

9. The powered ophthalmic device of claim 1 wherein the lens is a contact lens.

10. The powered ophthalmic device of claim 1 wherein the lens is selected from the group consisting of IOL's, contact lenses, onlays and inlays.

11. A powered ophthalmic device, the powered ophthalmic device comprising:
- a lens;
- a power source incorporated into the lens;
- an extreme gaze angle detection system incorporated into the lens, the extreme gaze angle detection system having a sensor to detect at least one of upper and lower vertical angles of extreme gaze, medial and lateral angles of extreme gaze, a lens actuator, cooperatively associated with the sensor and configured to receive and assess input from sensor and implement a lens function in in response to a detection of an extreme gaze angle between negative 25 and negative 30 degrees from horizontal or between 10 to 15 degrees from horizontal wherein the power source powers the extreme gaze angle detection system and the lens actuator.

* * * * *